United States Patent
Rimando et al.

(10) Patent No.: US 8,133,917 B2
(45) Date of Patent: Mar. 13, 2012

(54) PTEROSTILBENE AS AN AGONIST FOR THE PEROXISOME PROLIFERATOR-ACTIVATED RECEPTOR ALPHA ISOFORM

(75) Inventors: Agnes M. Rimando, Oxford, MS (US); Dennis R. Feller, Oxford, MS (US); Wallace H. Yokoyama, Berekley, CA (US)

(73) Assignees: The United States of America as represented by the Secretary of Agriculture, Washington, DC (US); The University of Mississippi, University, MS (US)

( * ) Notice: Subject to any disclaimer, the term of this patent is extended or adjusted under 35 U.S.C. 154(b) by 0 days.

(21) Appl. No.: 12/911,376

(22) Filed: Oct. 25, 2010

(65) Prior Publication Data

US 2011/0060060 A1 Mar. 10, 2011

Related U.S. Application Data

(62) Division of application No. 11/207,038, filed on Aug. 18, 2005, now abandoned.

(60) Provisional application No. 60/602,784, filed on Aug. 19, 2004.

(51) Int. Cl.
*A61K 31/075* (2006.01)
*A61K 38/00* (2006.01)
*A01N 65/00* (2009.01)

(52) U.S. Cl. .......................... 514/720; 514/7.4; 424/732
(58) Field of Classification Search ........................ None
See application file for complete search history.

(56) References Cited

U.S. PATENT DOCUMENTS

2005/0038125 A1 * 2/2005 Smit et al.

* cited by examiner

*Primary Examiner* — Michele Flood
(74) *Attorney, Agent, or Firm* — John D. Fado; Evelyn M. Rabin

(57) ABSTRACT

Resveratrol, a stilbenoid antioxidant found in grapes, wine, peanuts and other berries, has been reported to have hypolipidemic properties. Resveratrol and its three analogs (pterostilbene, piceatannol and resveratrol trimethyl ether) were evaluated for their effects on the activation of the peroxisome proliferator-activated receptor alpha (PPARα) isoforms, a receptor shown to mediate the activity of lipid-lowering drugs such as the fibrates. The four stilbenes and ciprofibrate (positive control) were evaluated for the activation of endogenous PPARα in H4IIEC3 cells. Pterostilbene demonstrated the highest induction of PPARα demonstrating increases of 7- and 9-14 fold relative to control. The maximal responses to pterostilbene are similar to those obtained with the hypolipidemic drug, ciprofibrate; that is, pterostilbene acts as a PPARα agonist, like that of the fibrate class, and is a more effective hypolipidemic agent than resveratrol.

3 Claims, 2 Drawing Sheets

| | $R_1$ | $R_2$ | $R_3$ | $R_4$ |
|---|---|---|---|---|
| Resveratrol | OH | OH | OH | H |
| Pterostilbene | OCH$_3$ | OCH$_3$ | OH | H |
| Piceatannol | OH | OH | OH | OH |
| Reveratrol trimethylether | OCH$_3$ | OCH$_3$ | OCH$_3$ | H |

Ciprofibrate

PTEROSTILBENE AS AN AGONIST FOR THE PEROXISOME PROLIFERATOR-ACTIVATED RECEPTOR ALPHA ISOFORM

REFERENCE TO RELATED APPLICATION

This application is a divisional application of application Ser. No. 11/207,038, filed Aug. 18, 2005, now abandoned, which claims the benefit of U.S. Provisional Application No. 60/602,784, filed Aug. 19, 2004, which is incorporated herein by reference in its entirety.

BACKGROUND OF THE INVENTION

1. Field of the Invention

This invention relates to pterostilbene, an analog of resveratrol, found in grapes, wine, peanuts and other berries. Pterostilbene activates the peroxisome proliferator-activated receptor alpha (PPARα) isoform, a receptor proposed to mediate the activity of lipid-lowering drugs. As a PPARα agonist, pterostilbene is capable of acting as an effective hypolipidemic agent.

2. Description of the Relevant Art

The peroxisome proliferator-activated receptor (PPAR) isoforms are members of the nuclear receptor superfamily of ligand-activated transcription factors. They were first identified in *Xenopus* frogs as receptors that induce the proliferation of peroxisomes (Dreyer et al. 1992. *Cell* 68: 879-887). Three PPAR isoforms are known: PPARα, PPARγ, and PPARδ. The PPARs control gene expression by interaction with specific response elements in the promoter region of target genes (Tugwood at al. 1996. *Ann. New York Acad. Sci.* 804: 252-265). The PPARs play a central role in carbohydrate and lipid homeostasis, and govern other biological processes such as energy metabolism, cell proliferation and differentiation, and inflammation (Chakrabarti and Rajagopalan. 2004. *Curr. Med. Chem.: Immunol. Endocr. Metab. Agents* 4: 67-73; Escher and Wahli. 2000. *Mutation Res.* 448: 121-138; Gilde and Van Bilsen. 2003. *Acta Physiol. Scand.* 178: 425-434; Kersten, S. 2002. *Eur. J. Pharmacol.* 440: 223-234; Mudaliar and Henry. 2002. *Curr. Opin. Endocrinol. Diabetes* 9: 285-302). The PPARs are also suggested to play a role in the pathogenesis and proliferation of colorectal (Jackson et al. 2003. *Gut* 52: 1317-1322) and lung (Inoue et al. 2001. *Anticancer Res.* 21: 2471-2476) tumor progression possibly via inhibition of proliferation. The PPARα isoform, predominantly involved in fatty acid and lipid catabolism and import, activates genes involved in fatty acid oxidation in the liver, heart, kidney, and skeletal muscles (Fruchart et al. 2003. *Prog. Exper. Cardiol.* 8: 3-16; Gilde and Van Bilsen, supra). In the liver, activation of PPARα leads to increased β-oxidation of fatty acids and decreased triglyceride-VLDL synthesis (Fruchart and Duriez. 2004. *Ann. Pharmaceut. Franc.* 62: 3-18). Activation of PPARα also leads to the reduction of triglyceride because of repression of hepatic apolipoprotein C-III and to the increase in lipoprotein lipase gene expression (Gervois et al. 2000. *Clin. Chem. Lab. Med.* 38: 3-11). Furthermore, PPARα activation causes induction of hepatic apolipoprotein A-I and A-II expression, in humans, leading to increased plasma HDL cholesterol. PPARα agonists also slow down the progression of premature coronary atherosclerosis (Fruchart et al. 2003, supra) and have been demonstrated to regulate metabolism of amino acids in the liver (Kersten et al. 2001. *FASEB J.* 15: 1971-1978).

Resveratrol is a well-known antioxidant (Stivala et al. 2001. *J. Biol. Chem.* 276: 22586-22594; Teguo et al. 1998. *J. Nat. Prod.* 61: 655-657) and cancer chemopreventive compound (Jang et al. 1997. *Science* 275: 218-220) present in grapes and wine. Its occurrence in wine has been linked to low incidence of fatal coronary heart disease among populations consuming wine moderately (Hegsted and Aussman. 1988. *J. Nutr.* 118: 1184-1189; Renaud and De Lorgeril. 1992. *Lancet* 339:1523). Dietary resveratrol at 50 ppm suppressed the blood serum lipid peroxidase levels in rats, and dose-dependently suppressed serum triglyceride and very-low-density lipoprotein-(VLDL-) and low-density-lipoprotein-(LDL-) cholesterol levels (Miura et al. 2003. *Life Sci.* 73: 1393-1400).

Pterostilbene is another grape compound that also was found to have antioxidant (Rimando et al. 2002. *J. Agric. Food Chem.* 50: 3453-3457; Stivala et al., supra) and cancer chemopreventive property similar to resveratrol (Rimando et al., supra). Pterostilbene has antidiabetic (Manickam et al. 1997. *J. Nat. Prod.* 60: 609-610) properties, and inhibits the enzymes cyclooxygenase-1 (COX-1) and COX-2, inferring anti-inflammatory properties (Likhitwitayawuid et al. 2002. *Planta Medica* 68: 841-843). Furthermore, pterostilbene is cytotoxic to a number of cancer cell lines in vitro (Rimando et al. 1994. *Nat. Prod. Lett.* 4: 267-272).

Like resveratrol and pterostilbene, piceatannol, has a cancer chemopreventive property (Waffo-Teguo et al. 2001. *Nutrition and Cancer* 40: 173-179), and is a stronger antioxidant than resveratrol and a potent anti-arrhythmic agent (Hung et al. 2001. *Free Radical Biol. Med.* 30: 877-883; Lee et al. 1998. *Combinat. Chem. High Throughput Screen* 1: 35-46). The cytochrome P450 enzyme CYP1B1 metabolizes resveratrol to piceatannol, demonstrating that a natural cancer chemopreventive agent can be converted to an anticancer compound by an enzyme which is over expressed in a wide variety of human tumors (Potter et al. 2002. *Brit. J. Cancer* 86: 774-778). Piceatannol showed anti-allergic effects in experimental models of type I allergy (Matsuda et al. 2001. *Biol. Pharm. Bull.* 24: 264-267). It has also been shown to induce apoptotic cell death in BJAB lymphoma cells with activity equal to resveratrol. Piceatannol also induced apoptosis in ex vivo assays with leukemic lymphoblasts, whereas resveratrol did not (Wieder et al. 2001. *Leukemia* 15: 1735-1742). Resveratrol trimethylether was found to be more cytotoxic than resveratrol in cultured human lung and colon cancer cells (Lee et al. 2003. *Arch. Pharm. Res.* 26: 253-257).

Thus, in view of reports on the hypolipidemic property of resveratrol, the three analogs were of interest because their biological activity profiles are similar to that of resveratrol and in some assays are reported to be more potent than resveratrol. The goal of this work was to investigate whether these analogs are PPARα activators.

SUMMARY OF THE INVENTION

We have investigated the property of pterostilbene as an agonist of PPARα and have determined that pterostilbene can be used as a hypolipidemic agent.

In accordance with this discovery, it is an object of the invention to provide a pharmaceutical composition that acts as a hypolipidemic agent.

It is a further object of the invention to provide a pharmaceutical composition that specifically activates PPARα.

In particular, this invention provides a method of treating dyslipidemias in individuals at risk of cardiovascular disease by administering a pharmaceutical composition containing pterostilbene.

It is further part of this invention to provide a method of lowering cholesterol levels in individuals by administering a pharmaceutical composition containing pterostilbene.

Also part of this invention is a kit, comprising a pharmaceutical composition containing pterostilbene; and instructions for the use of the kit.

Other objects and advantages of this invention will become readily apparent from the ensuing description.

DETAILED DESCRIPTION OF THE INVENTION

Figure 1:
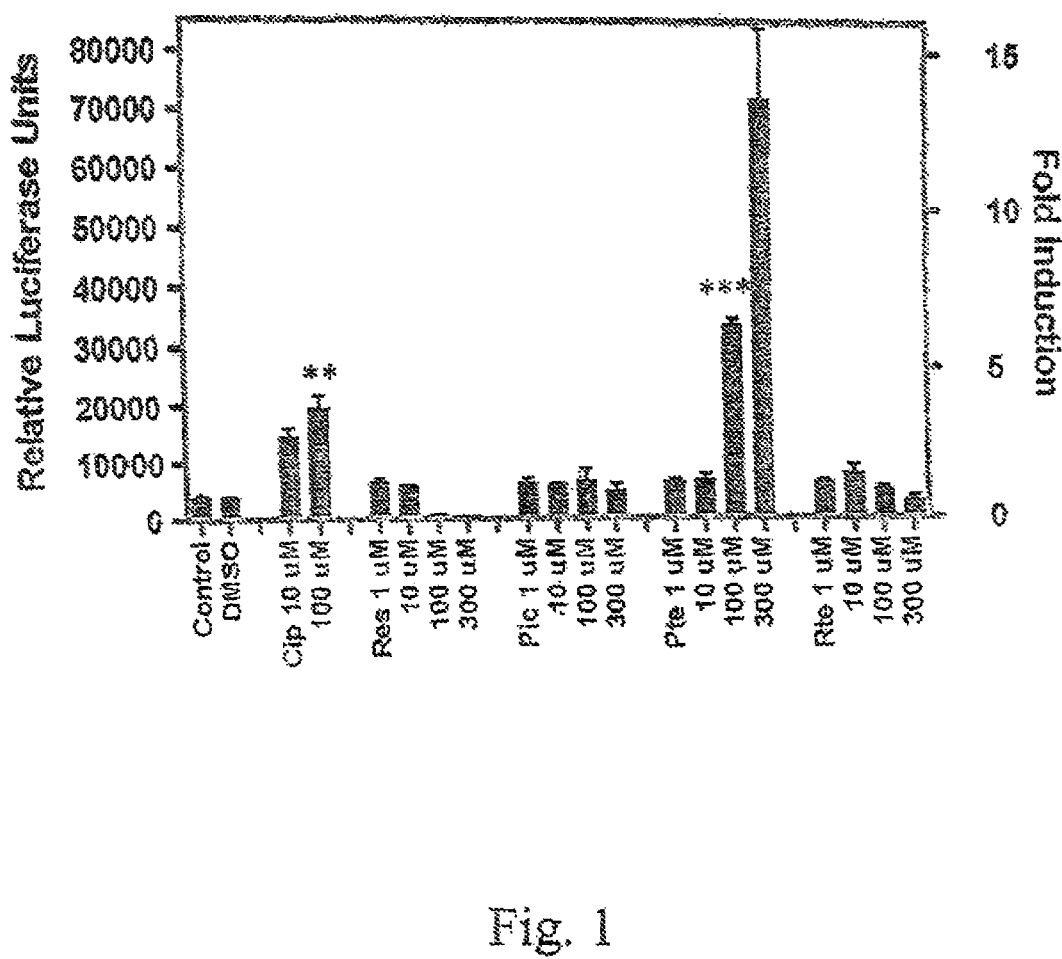
FIG. 1 shows the structures and formulae of resveratrol, pterostilbene, piceatannol, resveratrol trimethylether, and ciprofibrate.
Figure 2:
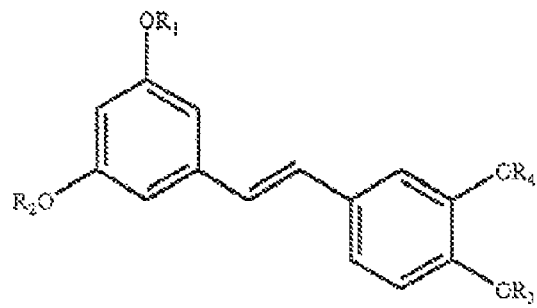
FIG. 2 shows the effect of stilbenes on PPARα in H4IIEC3 cells transfected with the PPRE-AB-luciferase reporter gene plasmid. Cip, ciprofibrate; Res, resveratrol; Pic, picetannol; Pte, pterostilbene; Rte, resveratrol trimethyl ether; ns, not significantly different from control, p>0.05; , significantly different from control, p=0.001; *, highly significantly different from control, p=0.0001; n=4.
Figure 2:
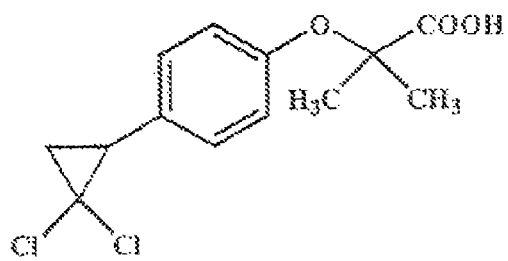

Dyslipidemias are disorders of lipoprotein metabolism, including lipoprotein overproduction or deficiency. These disorders may be manifested by elevation of the serum total cholesterol, low-density lipoprotein (LDL) cholesterol and triglyceride concentrations, and a decrease in the high-density lipoprotein (HDL) cholesterol concentration. Resveratrol has been shown to have hypolipidemic properties in rat feeding studies causing lowering of triglyceride (Miura et al., supra) and serum cholesterol levels (Miura of al., supra; Kollar et al. 2000. *Vnitmi Lekarstvi* 46: 856-860). On the contrary, a study in rabbits showed no difference in lipoprotein-cholesterol concentration between the control group and the group that received oral resveratrol (Wilson et al. 1996. *Life Sci.* 59: 15-21). Additionally, resveratrol promoted atherosclerotic development in these animals. On the basis of results of studies on the effect of resveratrol in human aortic cells, it was hypothesized that it may confer cardiovascular protection by functioning as a pleiotropic cellular effector (Wu of al. 2004. In: *Phytochemicals: Mechanisms of Action*, Meskin, M. S., ed., CRC Press LLC, Boca Raton, Fla., pages 145-161). Results from studies in Donyu rats showed the hypocholesterolemic activity of resveratrol to be due to increased excretion of neutral sterols and bile acids in the feces (Miura of al., supra).

"PPAR ligands or agonists" evolved as a group of structurally diverse compounds that activate these transcription factors, and emerged as an important class of therapeutic agents as PPARS have become an important molecular target to treat human metabolic disorders. PPARs play a central role in lipid homeostasis in regulating fatty acid metabolism and plasma lipoproteins. The fibrate drugs, such as ciprofibrate that was used in this study, were found to be ligands for PPARα and their activation of PPARα provided a mechanistic explanation for their clinical efficacy to treat cardiovascular diseases (Roberts and Moffat. 2001. *Comments on Toxicology* 7: 259-273).

Three analogs of resveratrol: pterostilbene, piceatannol and resveratrol trimethylether have been shown to exhibit some of the same biological activities as resveratrol; however, these analogs also have individual activities which they do not share with resveratrol. The capability of resveratrol and the analogs: pterostilbene, piceatannol and resveratrol trimethylether to affect PPARs, in particular, PPARα, and to thus affect lipid metabolism, was examined.

The finding that pterostilbene is an agonist for PPARα and that it possesses an activity comparable to a clinically prescribed hypolipidemic fibrate drug, provides a possible natural source alternative for the treatment of dyslipidemias. Whether or not resveratrol is a cholesterol lowering agent, the mechanism by which it does so does not appear to be via activation of PPARα, as is shown in this study. Results from this study suggest that pterostilbene may be a more effective hypolipidemic agent with differing mechanisms of lipid lowering action than that of resveratrol.

Pterostilbene has been reported in some small fruits such as grapes (Adrian et al. 2000. *J. Agric. Food Chem.* 48: 6103-6105) and berries of *Vaccinium* (Rimando at al. 2004. *J. Agric. Food Chem.* 52: 4713-4719) as well as in woody plants (Maurya at al. 1984. *J. Nat. Prod.* 47: 179-181; Arnone et al. 1977. *J. Chem. Soc. Perkins Trans.* 19: 2116-2118).

EXAMPLES

Having now generally described this invention, the same will be better understood by reference to certain specific examples, which are included herein only to further illustrate the invention and are not intended to limit the scope of the invention as defined by the claims.

Example 1

Analogs, Cell Lines, and Reagents

Resveratrol and piceatannol were commercial samples obtained from Sigma-Aldrich (St. Louis, Mo.) and Calbiochem (San Diego, Calif.), respectively. H4IIEC3 cells were obtained from the American Type Culture Collection (Rockville, Md.). The PPRE-AB luciferase gene reporter construct was obtained from Dr. Daniel J. Noonan (Department of Biochemistry, University of Kentucky, Lexington, Ky.). The luciferase assay kit was obtained from Promega Corporation (Madison, Wis.). NMR experiments were carried out on a Bruker Avance DRX (500 MHZ) instrument. PTLC, Merck Si gel F254 20×20 cm, 0.5 mm thick plate (VWR Scientific, Atlanta, Ga.). All solvents used were HPLC grade (Fisher Scientific, Suwanee, Ga.).

Pterostilbene and resveratrol trimethylether were prepared by partial methylation of resveratrol. To a solution of resveratrol (150 mg in 3.0 ml of MeOH) diazomethane was added dropwise, and the reaction was monitored by thin layer chromatography (TLC) for the methylated products. The reaction solution was dried under vacuum. The partially methylated products were purified by preparative TLC (developing solvent, hexane: ETOAc, 8:2; Rf 0.6 and 0.8 for pterostilbene and resveratrol trimethylether, respectively). The identity and structure of these compounds were confirmed by comparison with published spectroscopic data.

Example 2

Activation of PPARα in Rat Cells

Conditions for activation were essentially as described in Jaradat et al. (2002. *Planta Medica* 68: 667-671). Briefly, H4IIEC3 cells, a rat hepatoma cell line, were grown in a 150 mm Petri dish containing Dulbecco's Modified Eagle's Medium (DMEM) supplemented with 10% (v/v) fetal bovine serum. Upon reaching 75% confluency, cells were transfected with PPRE-AB (peroxisome proliferator response element with rat fatty acyl CoA β-oxidase AB promoter region sequence)—luciferase gene reporter construct, by electroporation (Square electroporator model T820) at 190 V for 70 msec and 1 pulse. Transfected cells along with the medium were plated in 96 well microtiter plates, at 100,000 cells/well. After 24 hr incubation, ciprofibrate at 10 and 100 µM, resveratrol and its three analogs at 1, 10, 100, and 300 µM, were added to the medium containing cells. FIG. 1 shows the structures and formulae of resveratrol, pterostilbene, piceatannol, resveratrol trimethylether, and ciprofibrate. After incubation with the test compounds for 30 hr, the cells were lysed and the luciferase activity of the supernatant was determined using a luminometer (Packard Instrument Company, Meriden, Conn.). Data were analyzed using GraphPad-Prism software.

Of the four stilbene analogs, pterostilbene demonstrated the highest induction of luciferase activity at 100 and 300 µM (FIG. 1). The maximal luciferase responses to pterostilbene at 100 and 300 µM were about 7 fold and 14 fold, respectively, when compared to the corresponding control values (n=4) in H4IIEC3 cells. The maximal luciferase activity responses to ciprofibrate at 100 µM was about 5 fold compared to control (n=4). These results showed that PPARα activation by pterostilbene (33910±788 relative luciferase units) is comparable to that of ciprofibrate (19460±1466 relative luciferase units) at 100 µM. Piceatannol and resveratrol trimethylether induced luciferase activity only slightly at all the concentrations tested. At 1 and 10 µM, pterostilbene, as well as resveratrol, only minimally induced luciferase activity. Resveratrol was toxic to H4IIEC3 cells at 100 and 300 µM. These results indicate that pterostilbene, like ciprofibrate, acts as an agonist of PPARα in H4IIEC3 cells, whereas the remaining stilbene analogs are not activators of PPARα.

Example 3

Effect of Pterostilbene and Resveratrol in in vivo Hamster Studies

Male golden Syrian hamsters (Charles River, Wilmington, Mass.), initial weight ranging from 34-41 g, were fed a powdered stock diet (Rodent Lab Chow 5001, Purina Mills, St. Louis, Mo.) for 7 days. The animals were placed in individual wire-bottom cages in a room kept at 20-22° C., 60% rh and 12 h light and dark cycle. Following the initial 7 day period, 8-10 animals were randomly assigned from a weight sorted list to each of five test diets (α-cellulose control and test substance). Food intake was measured twice each week and body weights were monitored once a week. After 21 days on the treatment diets, the animals were killed, blood was collected and analyzed for total cholesterol by the cholesterol oxidase method and lipoprotein cholesterol, by size exclusion chromatography, as previously described (German et al. 1996. Nutrition Res. 16: 1239-1249). All animal procedures were approved by the Animal Care and Use Committee, Western Regional Research Center, USDA, Albany, Calif. and conformed to the principles in "Guide for the Care and Use of Laboratory Animals" (Committee on Care and Use of Laboratory Animals 1985). Plasma blood glucose was determined using a blood glucose meter (Fast Glucose Meter-Precision Xtra, MediSense, Bedford, Mass., USA).

Diets were prepared by dissolving powdered cholesterol into warmed butterfat, followed by the addition of corn and fish oil. The small amounts of test ingredients were dissolved in about 50 ml of ethanol and added to the stirring dry ingredients. The liquid fat was also added to the dry ingredients while stirring. The composition is shown in Table 1.

TABLE 1

Composition of Diet

| Ingredient | Wt. (g) |
| --- | --- |
| Butterfat, anhydrous | 80 |
| Corn Oil | 100 |
| Fish Oil, Menhaden | 20 |
| Cholesterol | 1.5 |
| Cellulose, microcrystalline | 50 |
| Casein | 200 |
| Starch, corn | 497.5 |
| Methionine | 3 |
| Choline bitartrate | 3 |
| Mineral Mix | 35 |
| Vitamin Mix | 10 |
| Test Substance | 25 mg/kg |

Compared to the control group, plasma low density lipoprotein (LDL) cholesterol was 29% lower in the pterostilbene-fed group and 20% lower in the resveratrol-fed group, at 25 mg/kg diet (Table 2). Total plasma cholesterol was 18% lower with pterostilbene and 14% lower with resveratrol. LDL/HDL ratio was statistically significantly lower for pterostilbene but not for resveratrol, compared to control, at this diet concentration. Weight gain and HDL were similar for all groups. Compared to the control group, the plasma glucose level of only the pterostilbene-fed group was lowered.

TABLE 2

Effect of Pterostilbene and Resveratrol on Plasma Lipoprotein Cholesterol Levels in Hamsters

| | Control | | Pterostilbene* | | Resveratrol* | |
| --- | --- | --- | --- | --- | --- | --- |
| | AVG | SEM | AVG | SEM | AVG | SEM |
| | Plasma Lipoprotein Cholesterol (mg/dL) | | | | | |
| VLDL | 99.3 | 15.3 | 82.7 | 15.7 | 83.6 | 13.0 |
| LDL | 320.9 | 4.9 | 228.1 | 4.2 | 257.4 | 8.0 |
| HDL | 127.4 | 1.1 | 137.0 | 2.1 | 127.1 | 20.0 |
| Total | 547.6 | 6.7 | 447.8 | 5.6 | 468.2 | 8.7 |
| LDL/HDL | 2.6 | 0.37 | 1.8 | 0.39 | 2.2 | 0.62 |
| | Final Weights (g) | | | | | |
| Body wt | 100.9 | 2.0 | 110.5 | 2.7 | 109.5 | 3.2 |
| Liver wt | 6.6 | 0.18 | 7.9 | 0.28 | 7.6 | 0.33 |
| Liver/Body | 6.6 | 0.09 | 7.1 | 0.12 | 6.9 | 0.10 |
| Plasma glucose | 216.5 | 10.1 | 185.1 | 8.7 | 191 | 7.7 |
| N | 10 | | 8 | | 8 | |

*Concentration: 25 ppm

In addition, at the same time the feeding experiments with pterostilbene and resveratrol were done, two tomato and five eggplant varieties were also tested. Freeze-dried plant materials were fed at about 10% of total diet. Test substances (pterostilbene and resveratrol) were found to be more effective than the plant materials for lowering the plasma cholesterol levels (data not shown).

Differences between treatments were tested by two-tailed t-test assuming equal variance, and were considered significant at $p<0.05$.

All publications and patents mentioned in this specification are herein incorporated by reference to the same extent as if each individual publication or patent was specifically and individually indicated to be incorporated by reference.

It is understood that the foregoing detailed description is given merely by way of illustration and that modifications and variations may be made therein without departing from the spirit and scope of the invention.

We claim:

1. A method of lowering lipid levels in an individual comprising administering to an individual in need thereof a therapeutically effective amount of an edible pharmaceutical composition consisting of an edible therapeutically effective unit dosage of isolated or chemically-synthesized pterostilbene and a pharmaceutically acceptable carrier, wherein the unit dosage of pterostilbene administered orally is effective to lower lipid levels in an individual.

2. A method of treating dyslipidemias in an individual at risk of cardiovascular disease by administering to an individual in need thereof a therapeutically effective amount of an edible pharmaceutical composition consisting of an edible therapeutically effective unit dosage of isolated or chemically-synthesized pterostilbene for lowering lipid levels in an individual and a pharmaceutically acceptable carrier, wherein the unit dosage of pterostilbene administered orally is effective to treat dyslipidemias or reduce the risk of dyslipidemias in an individual.

3. A method of lowering lipid levels in an individual comprising administering to an individual in need thereof an effective amount of an edible nutraceutical composition consisting of an edible therapeutically effective unit dosage of isolated or chemically-synthesized pterostilbene and a nutraceutically acceptable carrier, wherein the unit dosage of pterostilbene administered orally is effective to lower lipid levels in an individual and to treat or reduce the risk of dyslipidemias in an individual.

* * * * *